May 25, 1976 W. E. LAMMERTS Plant Pat. 3,892
LILAC PLANT
Filed March 24, 1975
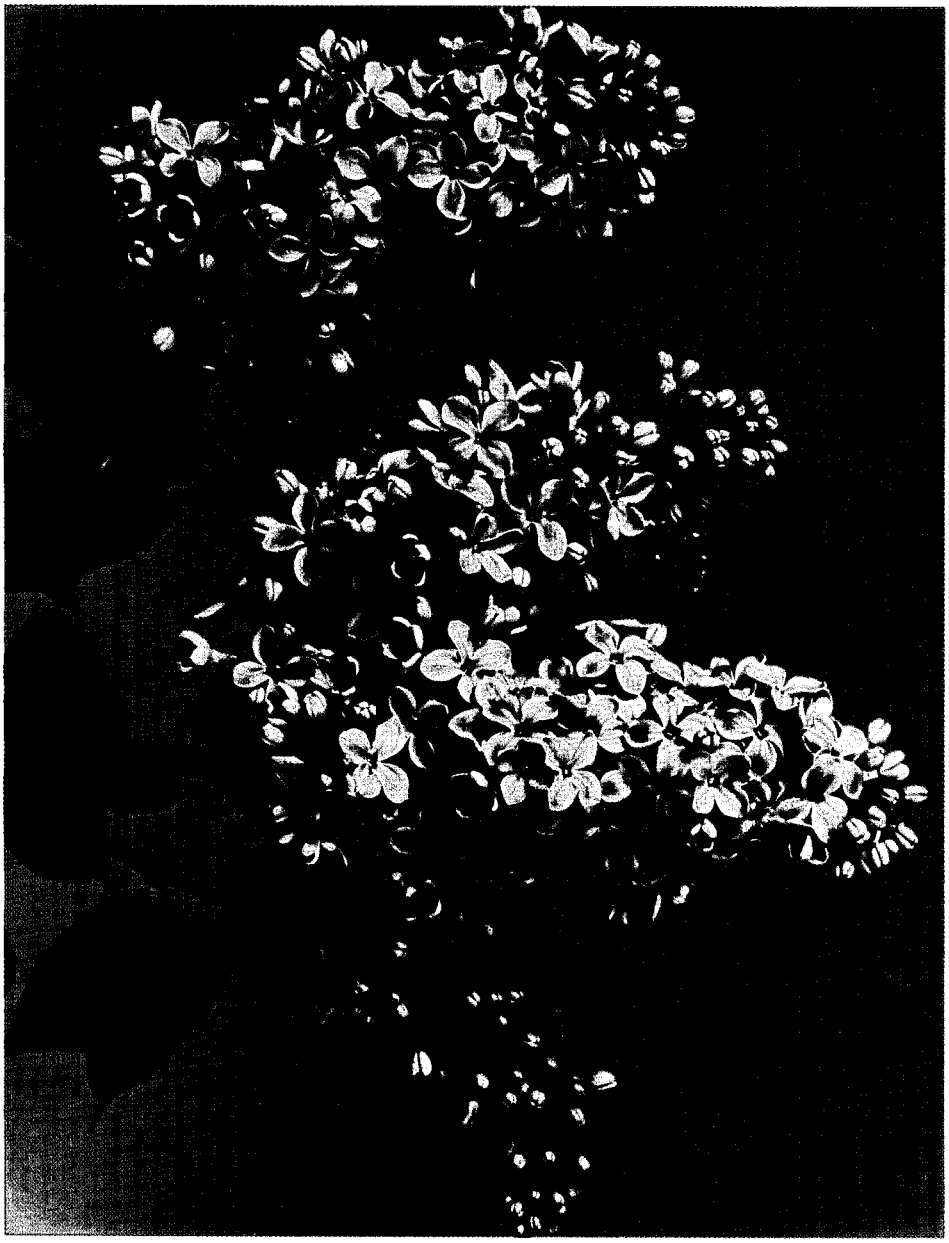

United States Patent

Plant Pat. 3,892
Patented May 25, 1976

3,892
LILAC PLANT

Walter E. Lammerts, Corralitos, Calif., assignor to Hines Wholesale Nurseries, Santa Ana, Calif.

Filed Mar. 24, 1975, Ser. No. 561,325
Int. Cl. A01h *5/00*
U.S. Cl. Plt.—66 1 Claim

The present invention relates to a new and distinct variety of lilac plant originated by me by crossing two unnamed and unpatented seedlings, each of which was derived from seedlings derived from various crosses I have made with seed of an unnamed and unpatented early-leafing variety identified by me in my breeding records by the identification number C112.

The primary objective in making this cross was to further and improve the objectives set forth in Plant Pat. 1,238 previously granted to me on Jan. 5, 1954. As set forth in this prior application, I had produced a lilac which would flower normally in Southern California and comparable climatic areas having short and mild winters. The present invention relates to a lilac plant which requires less than normal winter-chilling required by most lilacs, including the usual eastern lilacs, and still produces normal flowering bloom clusters.

My new variety is characterized by its ability to achieve normal flowering without requiring normal winter-chilling; by its regularity and abundance of bloom consisting of very large flower clusters measuring from 7 to 10 inches in length and from 7 to 12 inches in width; and by the size of relatively large florets, at times measuring from ⅞ of an inch to 1 3/16 inches in diameter. Occasional flower clusters will be as large as 12 inches in both length and width.

The new variety was asexually reproduced by me on cultivated property known as Descanso Distributors at Chino, Calif. Reproduction of this new variety was made by cuttings and also by budding to Ligustrum understock, and as a result established that the foregoing distinguishing characteristics come true to form and are established and transmitted through succeeding propagations.

The drawing which accompanies this petition shows a typical view of the flowers and foliage of my new lilac variety and is portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: Descanso Distributors Nursery in Chino, Calif.

Parentage: Seedling resulting from planned propagation.
- Seed parent.—A large petalled unpatented seeding of an unnamed early-leafing variety identified in my breeding records as C112, crossed to a seedling derived from seed obtainead by open pollenation of an unpatented variety, Syringa "Lamertine."
- Pollen parent.—A deep pink unnamed seedling derived from seed produced by open pollenation of a seedling of an unpatented variety, S. "Buffon," identified in my breeding records as 42–109–4.

The seed which were produced by this cross in 1950, were sown in 1951, and plants first bloomed in 1953.

Blooming habit: Early; usually from about the early part of march to mid-April in Southern California. In full flower and leaf by the end of March.

*The plant*

Form of plant: Bush.
Growth: Upright; vigorous, compact.
Branches:
- New growth is in the Red-Purple Group, Plates 59A to 59B.
- Mature growth is in the Greyed-Green Group, Plate 197C to Plate 197D.

Foliage:
- Size.—1⅞ to 2½ inches wide and from about 2¼ inches to 3 inches long.
- Quantity.—Abundant.
- Shape.—Ovate with an acuminate tip, and a cordate base. The leaf margin is entire.
- Venation.—Pinnate.
- Arrangement.—Opposite.
- Color.—New leaves are in the Greyed-Orange Group, Plates 177A to 177B with over-tones of red and greaen.
- Mature leaves.—Are in the Yellow-Green Group and vary from Plates 146A to 146B to 146C. There are still present red over-tones.

*The Flower*

Bud:
- Individual florets of cluster.
- Size.—Large.
- Form.—Short with a flat to an elongate tip.
- Color.—In the Red-Purple Group, Plate 70A.

Bloom: Individual florets of cluster, about ⅞ of an inch, to about 1¼ inches in diameter. Florets are borne in large clusters measuring from 7 to 10 inches in length and from 7 to 12 inches in width, with occasional clusters as large as 12 inches in both length and width. Individual raceme lengths comprising the cluster range from 2¾ inches to 3¼ inches in length.
- Color.—Open flowers are in the Purple Group, Plate 78B fading to Purple Group, Plate 78C. Underside of the flower is in the Red-Purple Group, Plates 70A to 70B. The edge of the flower has a very color line of Red-Purple Group, Plate 70D.

I claim:

1. A new and distinct variety of lilac plant, substantially as herein shown and described, characterized particularly as to novelty by its relatively short and mild winter-chilling requirements, by its regular and abundant production of large flower clusters consisting of large individual florets, by its vigorous habit of plant growth, and by its abundant production of large and attractive foliage.

No references cited.

ROBERT E. BAGWILL, Primary Examiner